(12) United States Patent
Vitti

(10) Patent No.: US 11,350,912 B2
(45) Date of Patent: Jun. 7, 2022

(54) FEMALE HEALTH TRACKING AND DIAGNOSIS METHOD

(71) Applicant: FLO Living LLC, New York, NY (US)

(72) Inventor: Alisa Vitti, New York, NY (US)

(73) Assignee: FLO Living LLC, New York, NY (US)

( * ) Notice: Subject to any disclaimer, the term of this patent is extended or adjusted under 35 U.S.C. 154(b) by 4 days.

(21) Appl. No.: 16/255,700

(22) Filed: Jan. 23, 2019

(65) Prior Publication Data

US 2019/0223843 A1    Jul. 25, 2019

Related U.S. Application Data

(60) Provisional application No. 62/620,770, filed on Jan. 23, 2018.

(51) Int. Cl.
| | |
|---|---|
| *G16H 50/20* | (2018.01) |
| *G16H 10/20* | (2018.01) |
| *A61B 10/00* | (2006.01) |
| *A61B 5/00* | (2006.01) |
| *A61B 5/16* | (2006.01) |
| *A61B 5/145* | (2006.01) |

(52) U.S. Cl.
CPC ........ *A61B 10/0012* (2013.01); *A61B 5/4306* (2013.01); *A61B 5/4839* (2013.01); *A61B 5/7435* (2013.01); *G16H 10/20* (2018.01); *G16H 50/20* (2018.01); *A61B 5/14532* (2013.01); *A61B 5/14546* (2013.01); *A61B 5/165* (2013.01); *A61B 2010/0029* (2013.01)

(58) Field of Classification Search
CPC .. A61B 10/0012; A61B 5/4306; G16H 10/20; G16H 20/00; G16H 50/20
USPC .................................................... 705/2
See application file for complete search history.

(56) References Cited

U.S. PATENT DOCUMENTS

| | | | |
|---|---|---|---|
| 2003/0120173 A1* | 6/2003 | Saini | A61B 10/0012 600/551 |
| 2005/0010128 A1* | 1/2005 | Shiraishi | G01N 33/528 600/551 |
| 2012/0209533 A1* | 8/2012 | Kodama | A61B 5/4866 702/19 |
| 2016/0140314 A1* | 5/2016 | Karchmer | A61B 5/01 600/33 |

FOREIGN PATENT DOCUMENTS

WO    WO-2014135699 A2 *    9/2014    ............. G16H 50/20

OTHER PUBLICATIONS

Satoshi Sohda. MD, PhD et al, Relationship between the menstrual cycle and timing of ovulation revealed by new protocol: Analysis of Data from a self-tracking health App, Nov. 19(11), 2017, e391, Journal of Medical internet Research (Year: 2017).*

Ying, Ying; Follicular phase length has no influence on frozen-thawed embryo transfers in natural cycles; : Journal of Ovarian Research 13 : 1-6. BioMed Central. (2020) (Year: 2020).*

* cited by examiner

*Primary Examiner* — Hiep V Nguyen
(74) *Attorney, Agent, or Firm* — Nolte Lackenbach Siegel

(57) ABSTRACT

A method, process, or software package configured to receive user inputs related to health, calculate a diagnosis based upon user inputs and historical data, calculate a treatment plan based upon user inputs and historical data, and present the diagnosis and a treatment plan to the user via a graphical user interface.

14 Claims, 2 Drawing Sheets

FEMALE HEALTH TRACKING AND DIAGNOSIS METHOD

CROSS-REFERENCE TO RELATED APPLICATIONS

This application claims priority to U.S. Provisional Patent Application having Ser. No. 62/620,770, which was filed Jan. 23, 2018. This priority application is hereby incorporated by reference in its entirety into the present application to the extent consistent with the present application.

BACKGROUND

World society has made impressive advancements in medicine in the past 50 years that have resulted in saving lives, improved quality of life, and increased average life span. For example, fifty years ago, the leading cause of death in the United States was heart disease, as it is today, but the death rate was nearly three times higher—559 deaths per 100,000 in 1965 compared to 192 deaths per 100,000 in 2014. Similarly, comparing to 1960, the survival rate for cancer is at least 30 percent higher today and life expectancy (in the U.S.) was 68 where it is now nearly 80. The 1960s started major advances in our understanding of the genetic code and transfer RNA, building on Watson and Crick's 1953 discovery of DNA's molecular structure and setting the stage for the exciting fields of genomics, epigenomics and bioengineering. The 1960s saw the development of the first artificial heart and the balloon embolectomy catheter that allowed the first minimally invasive surgical procedure. Surgeons attempted the first human liver and heart transplants, procedures that now save thousands of lives each year. Vaccines for rubella and mumps introduced in the 1960s have largely eradicated those diseases in the U.S. Scientists first made synthetic insulin in a laboratory in the 1960s. A decade later, commercial production of synthetic insulin made lifesaving treatment available to people with diabetes across the country. These medical advancements continued through the 1990s and into the 21st century with the completion of the Cancer Genome Atlas that provided a compilation of genomic changes in all cancers that serves as the source book for treatment, the introduction of targeted biopharmaceuticals, the improvement of successful HIV and hepatitis C treatments, and pediatric vaccines.

Although these medical advancements are impressive, improved treatment for women's hormonal health has generally remained stagnant despite statistics showing that nearly 75% of women suffering from chronic women's menstrual and/or hormonal health issues. Exemplary women's hormonal and menstrual health issues include fibroids, premenstrual syndrome, premenstrual dysphoric disorder, polycystic ovary syndrome, ovarian cysts, endometriosis, heavy periods, missing periods, irregular cycles, cystic breasts, inability to conceive naturally, miscarriages, pediatric health problems, challenges with losing weight naturally gained during pregnancy, fatigue, insomnia, depression, thyroid hypothyroidism or hyperthyroidism, anxiety, mood swings, lack of sexual thoughts or low sex drive/desire, inability to reach orgasm or attain the sensations the body once had during orgasm, and difficulty with perimenopause or menopause. Further exemplifying the problem: Over twenty million women suffer from polycystic ovary syndrome (PCOS), fibroids, endometriosis, painful/difficult/heavy periods, and thyroid and adrenal issues; One in nine women suffers from PCOS; Fibroids occur in three out of every ten women over the age of thirty-five; About one in ten, or over eight million, U.S. women have endometriosis; Thirteen million Americans have underactive thyroid function, only half of whom have been correctly diagnosed; Women are five times more likely than men to be diagnosed with hypothyroidism; One in eight couples is infertile; Fibrocystic breasts affect 20 to 40 percent of menstruating women; An estimated seven million women meet the diagnostic criteria for clinical depression; and every ten minutes, twelve hysterectomies are performed in the United States, which is approximately six hundred thousand every year.

These statistics clearly show that women's menstrual and hormonal health is at or near crisis stage and the most problematic aspect is that the traditional treatment that has been overwhelmingly prescribed for many of these women's menstrual or hormonal issues since as early as 1965 has been the birth control pill, which is generally described as a mix of artificial estrogen and progesterone that modifies the bodies endocrine system to trick a woman's body hormonally into preventing ovulation and thus preventing pregnancy. The hormones in the pill have also shown to cause a thickening of the mucus around the cervix, which makes it more difficult for sperm to enter the uterus to fertilize any eggs that may have been released. Although the synthetic hormones introduced into women's bodies by the pill have shown to be successful in preventing pregnancies and treating the symptoms of several menstrual or hormonal health-related issues, the predominant use of the pill in society has caused a silent epidemic in women's hormonal health, as the natural hormonal balance of women has been destroyed by the mass introduction of the synthetic hormones by the pill. Women's natural body cycle and their endocrine systems have essentially been remapped by the synthetic hormones in the pill to the point where women's bodies are incapable of naturally, managing their own healthy hormone balance. Nevertheless, prescription rates of the pill have continually increased over the past 50 years, as society appears to place more value on preventing an unwanted pregnancy that is does treating legitimate women's menstrual or hormonal health issues.

Further, the pill is nearly always prescribed to treat the symptoms of women's hormonal or menstrual health issues without the pill actually having the ability to treat the cause of the hormonal or menstrual health issue. For example, the pill has shown to mask symptoms of health issues related to serious health issues with women's ovaries, kidneys, liver, heart, and the quality of women's blood. The pill also changes a woman's brain chemistry and alters the way the mind communicates with the body, which can have serious consequences for a woman's physical health, moods, weight, libido, and personal relationships. As a specific example, the pill is often prescribed to minimize the painful symptoms of endometriosis, yet the pill has no impact on the actual cause of the endometriosis pain (the excess growth of endometrium lining outside the uterus), which can be cured with proper hormone balance.

Various software packages have been provided in the prior art to assist women in tracking hormonal health and menstrual cycle characteristics. However, the prior art software packages generally offer only vague or approximate cycle tracking, i.e., generally indicating two women when their menstrual cycle might start, when the cycle may end, and when they can expect ovulation to occur. None of the conventional software packages offer the ability to accurately predict the phases of a woman's menstrual cycle or to diagnose a woman's current hormonal or endocrine system balance and offer a corresponding recommended treatment plan to address the determined imbalance. Further, a woman's cycle timing can be impacted by a multitude of variables and conventional software packages are only capable of calculating cycle timing based on a user's initial inputs and are not able to dynamically calculate changes in a woman's cycle timing based on the woman's current health and hormonal symptoms. Further still, current software packages have no capability to diagnose or recommend treatment plans, such as nutrition or exercise that is calculated to remedy a woman's current challenges with her menstrual cycle.

As such, there is a need for a method for diagnosing and treating women's health issues that focuses on maintaining a woman's natural hormone balance and a healthy endocrine system without the introduction of artificial hormones or chemicals into a woman's body.

SUMMARY

Embodiments of the disclosure may provide a method, process, or software system that proactively manages women's hormonal, menstrual, and reproductive health. The method, process, or software system may provide for diagnosing and treating women's health issues with a focus on maintaining a woman's natural hormone balance and a healthy endocrine system without the introduction of artificial hormones or chemicals into a woman's body.

Embodiments of the disclosure may provide a method, process, our software package configured to receive a plurality of inputs from a user, wherein the plurality of inputs correspond to physical and mental indicators or symptoms that a woman may be encountering. The plurality of inputs may be processed by a microprocessor in communication with a memory device having a plurality of historical data thereon to algorithmically determine the woman's current hormone or endocrine system imbalance and recommend a treatment plan to rebalance the woman's hormone or endocrine system.

Embodiments of this disclosure may further provide a method, process, or software system configured to dynamically update a woman's diagnosis and treatment plan based upon current inputs and historical data related to the woman's hormones or endocrine system. The dynamic update may generally correspond to instances where a woman inputs additional symptoms or data into the innovation of the present disclosure that may then be algorithmically processed to identify and treat a new or varied condition.

Embodiments of this disclosure may further provide a method, process, or software system configured to generate updates relating to a woman's menstrual cycle and communicate those updates to selected users. The selected users may include significant others, spouses, friends, family members, or other members that may benefit from knowing a woman's current state in her cycle.

Embodiments of this disclosure may further provide a method, process, or software system configured to generate a nutrition plan for a woman based upon current and historical data relating to the woman cycle, symptoms, and physical activity, wherein the nutritional plan is specifically calculated using current and historical data to maintain the woman's endocrine system in hormonal balance.

Embodiments of the disclosure may further provide a method for diagnosing, treating, and tracking women's hormonal health. The method may include receiving cycle inputs from a user via an input device, the inputs representing hormonal data related to a menstrual cycle, transmitting the cycle inputs to a processor and storing the cycle inputs in a memory in electrical communication with the processor and initially calculating the timing and duration of at least three phases of the user's menstrual cycle using the cycle inputs. The method may further include displaying the calculated at least 3 phases of the user's cycle to the user on a graphical user interface, receiving symptom inputs from the user via the input device, the symptom inputs representing medical, emotional, or hormonal symptoms related to the user's menstrual cycle, and the symptom inputs being transmitted to the processor and stored in the memory, recalculating, with the processor, the at least 3 phases of the user's cycle based on the cycle inputs and the symptom inputs, generating, with the processor, a nutritional treatment plan calculated to remedy the medical, emotional, and hormonal symptoms, and displaying the recalculated at least three phases of the user's cycle and the nutritional treatment plan to the user on the graphical user interface.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
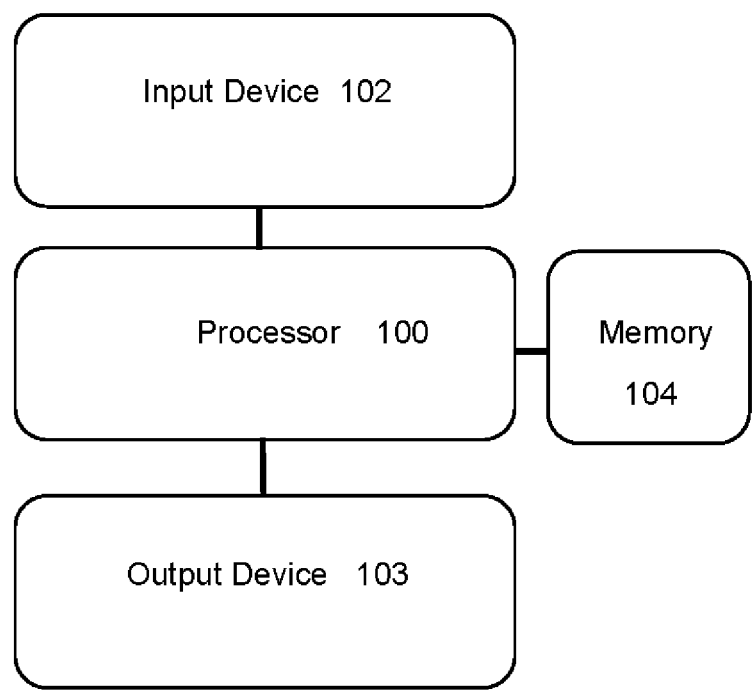
FIG. 1 illustrates an exemplary hardware configuration that may be utilized to implement various embodiments of the present disclosure.

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the various Figures. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Finally, the exemplary embodiments presented below may be combined in any combination of ways, i.e., any element from one exemplary embodiment may be used in any other exemplary embodiment, without departing from the scope of the disclosure.

Additionally, certain terms are used throughout the following description and claims to refer to particular components. As one skilled in the art will appreciate, various entities may refer to the same component by different names, and as such, the naming convention for the elements described herein is not intended to limit the scope of the invention, unless otherwise specifically defined herein. Further, the naming convention used herein is not intended to distinguish between components that differ in name but not function. Additionally, in the following discussion and in the claims, the terms "including" and "comprising" are used in an open-ended fashion, and thus should be interpreted to mean "including, but not limited to." All numerical values in this disclosure may be exact or approximate values unless otherwise specifically stated. Accordingly, various embodiments of the disclosure may deviate from the numbers, values, and ranges disclosed herein without departing from the intended scope. Furthermore, as it is used in the claims or specification, the term "or" is intended to encompass both exclusive and inclusive cases, i.e., "A or B" is intended to be synonymous with "at least one of A and B," unless otherwise expressly specified herein.

Turning to embodiments of the present disclosure, a women's hormones affect everything in her body in one way or another. For example, women may struggle with acne, oily hair, dandruff, dry skin, cramps, headaches, irritability, exhaustion, constipation, irregular cycles, heavy bleeding, clotting, shedding hair, weight gain, anxiety, insomnia, infertility, lowered sex drive, or bizarre food cravings, all as a result of hormone imbalance. The present disclosure provides a method, process, and/or software to manage a women's hormones that terminates external interference with a woman's natural hormonal balance, which eliminates both the symptoms and the root cause of the imbalance, and further then proactively cares for and maintains a hormonal baseline balance to promote long term endocrine system health. The inventive method, process, and/or software accomplishes this in two major ways: First, unlike conventional treatment regimes, the inventive concept addresses and treats the underlying reason or cause for the hormonal imbalance (not just the symptoms) and thus corrects the root or foundation of the problem; and second, the inventive concept further focuses on proactively addressing women's health issues by analytically determining and recommending nutritional and physical treatments that are calculated to maintain the endocrine system in optimal functioning condition.

A foundational aspect of the method, process, and/or software of the present disclosure is the medical fact that hormones seek balance and when the body's endocrine system that governs hormones is disrupted, the body will present one symptom, then another, then another, until the body generates or exhibits a full on health condition. The conditions that women exhibit might be different from one female to the next, based on genetic predisposition and lifestyle factors, but focusing on the symptoms and/or the conditions is far less valuable than addressing the underlying causes of the symptoms. By going to the root cause of endocrine system disruption and determining a proper regime of treatment, the method, process, and/or software of the present disclosure can actually trigger the endocrine system to get itself into healing mode and start functioning the way it was naturally intended. This results from the natural order and logic to how the body's endocrine system works.

The method, process, and/or software of the present disclosure will also serve as a touchstone for gynecologists, endocrinologists, and IVF specialists who want to "prescribe" the inventive method to patients as a complementary and integrative solution to addressing the root causes of hormone imbalance symptoms commonly observed in medicine. To raise standard gynecological care, women and gynecologists must begin to collaborate where they can so that medicine of the future can be a hybrid form, one in which people take greater responsibility for their own health instead of relying exclusively on doctors and hormonal supplements to make them better when they get sick. In this new hybrid, people will seek out a stronger understanding of how their bodies work and what they need to do to take care of themselves on a day-to-day basis. When medical issues arise, they can reach out to a team of wonderful practitioners in a variety of different specialties for guidance. Patients will know where they need to go to get the right information and won't expect one practitioner to have all the answers and, most important, they'll know how to listen to their bodies to guide them toward finding the solutions they need.

The innovation of the present disclosure provides a method, process, and/or software package that generally operates to receive several inputs from a user and build a database of current and historical user information based on the inputs. Thereafter, current user input information combined with historical information contained in the database are used to dynamically generate daily treatment, nutrition, or activity plans that are configured to provide the optimal endocrine system balance for the user. These dynamically generated daily treatment, nutrition, or action plans are algorithmically calculated by the innovation of the present disclosure using all of the information available to it, i.e., current or daily user input, most recent user input, historical user input that shows trends, and various databases containing symptom indicators for conditions that are treatable by the innovation of the present disclosure. As such, one of the primary aspects of the present innovation is the data input received from the user, as this data forms the foundation for both current and historical information that is used to generate treatments, nutritional recommendations, and action plans that are specifically calculated to balance hormonal levels in the endocrine system. Therefore, the following paragraphs describe a number of exemplary data inputs that may be provided to the innovation of the present disclosure by the user, and thereafter algorithmically processed to generate custom and dynamic treatments, nutrition recommendations, and action plans for the user.

The method, process, and/or software of the present disclosure is focused on one of the most essential and easily disturbed underlying causes of hormonal issues, the body blood sugar level, as stabilizing blood sugar is a fundamental step in a balanced and health endocrine system. Many patients wonder what the relationship between blood sugar and feminine/gynecological health is, and the answer under the present disclosure is "everything." It has been shown that a woman's endocrine system performs all of its complex functions via the language of hormones, and one of its main functions, first and foremost, is transporting glucose to the brain, muscles, and heart. If anything within that process is unbalanced, then the body will have mismanaged blood sugar as the first problem; as a result, though, none of the other parts of the endocrine system will function in a balanced manner either. Specifically, if the body's blood sugar is not properly balanced, then balancing the adrenals and avoiding adrenal fatigue will also be problematic if not impossible. Further, nearly every patient with women's health issues has blood sugar balance issues, and as such, one portion of various embodiments of the method, process, and/or software of the present disclosure focuses on the women's body blood sugar levels in order to obtain balanced hormones and a balanced body for good health.

The body breaks down carbs into glucose, so managing blood sugar under the present disclosure generally includes monitoring and responding to the body's glucose levels, moment to moment, and implementing the necessary steps to keep the glucose levels on a balanced or even keel. This generally means that the method, process, and/or software of the present disclosure carefully considers various inputs, known data, and user symptoms, activities, and nutrition to recommend foods and/or nutrition to balance glucose levels in the body. Exemplary inputs used to calculate balanced glucose levels (blood sugar) include the period start date, which is partially used to determine the phase of the menstrual cycle, the current and/or most recent symptoms of the body input by the user that indicate changes or elevated/decreased blood sugar levels, the calculated or inputted type of burner a body is (metabolic rate, which is also calculated from a plurality of parameters/symptoms including ease of losing weight, anxious feelings, dizziness, headaches, overheating, feel irritable or foggy-headed, and feeling cold in the fingers and toes), and known data related to blood sugar and the body's consumption thereof. Generally speaking, the innovation of the present disclosure may be configured to infer the body's blood sugar levels from input data, i.e., food, exercise, etc. However, in one embodiment of the present disclosure the innovation of the present disclosure may be configured to communication (via wireline, RF, Bluetooth, etc.) with a non-invasive mobile blood sugar sensor. This mobile sensor may be mounted in the back face of a watch, in a mobile phone, or in any other device capable of containing an optical (or other type) of sensor capable of measuring a blood sugar level. These parameters are used to calculate or determine, through an analytical process, nutrition and/or physical activity that will balance the blood sugar levels in the body to facilitate hormonal and endocrine system balance.

For example, if a woman eats a larger than normal portion of brown rice, sweet potatoes, or pasta and the body represents lethargic feelings, then the method, process, and/or software of the present disclosure will use this information, which is generally input by the user as a symptom or other data point, as inputs to calculate a recommended action to counteract the glucose level increase. The recommended action is essentially calculated to bring the body's glucose levels back into balance by, for example, recommending moderate exercise to deplete some of the glucose in the body to minimize the amount of corresponding insulin that the body will need to produce to process and appropriately store the glucose in the liver and cells as a result of the food ingested. By recommending moderate exercise when the body shows symptoms of high blood sugar or when the innovation of the present disclosure determines that a high glucose level is likely, the method, process, and/or software of the present disclosure substantially reduces the glucose imbalance in the blood stream and minimizes the associated hormone imbalance, as the body's muscles burn the glucose as fuel or energy before the body needs to generate insulin to support converting and storing the excess glucose in the body's liver and cells. Since the body's entire endocrine system relies on the glucose levels hugging a stasis line as closely as possible, the body perceives mismanaged blood sugar as a stressor. This, in turn, sends the body's adrenals into overdrive and they begin to generate cortisol and adrenaline, which causes the corresponding generation of off-kilter hormones.

Upon receiving the above noted data inputs, the method, process, and/or software of the present disclosure may algorithmically calculate and recommend the following activities to balance blood sugar. In the morning, after a brisk walk 20-minute walk, immediately drink at least 8 ounces of water. Eat breakfast within ninety minutes of waking and do not consume caffeine of any kind before eating breakfast, and eat a protein-rich food with breakfast, such as eggs, a vegan protein shake, or smoked salmon. Minimize carbohydrates to 30 grams in the morning for low metabolic rates and no more than 50 grams for fast burners.

Assuming there are no changes in the protocol (additional symptoms entered into the method, process, or software of the present disclosure), then lunch may be calculated algorithmically and recommended as follows. Eat lunch within three and a half hours of breakfast and consume the majority of daily calories at lunch. Try to consume only one complex carbohydrate and incorporate at least one good-fat food, such as avocado, olive oil, or sunflower seeds, as these keep blood sugar more stable and prevent the body from craving simple carbs later in the day. Take a digestive enzyme (a form of nutritional supplement) so the body can absorb as much nutrition as possible from the body's meal. The protocol may also recommend eating a midafternoon snack within two and a half to three and a half hours of lunch, which may be recommended as a nutrient-dense snack that will keep the body satisfied until dinner. Finally, the protocol may recommend eating dinner within two and a half to three and a half hours of the afternoon snack, where the dinner meal consists of vegetarian or animal protein and raw or cooked vegetables. The protocol may recommend avoiding grains and sugar of any other kind to reduce these carbs being stored as fat rather than being used for energy. Again, these recommendations may be calculated and presented at the beginning of the day, however, if the user of the present innovation enters additional data or symptoms after the morning calculations and recommendations, then the innovation may recalculate the recommendations to take the new data or symptom into consideration and to recommend nutrition or physical activity modifications to address or cure the newly inputted data or symptoms.

Although society and the medical community most commonly associates the adrenals with stress, they have a variety of other important functions in the body. To better understand all that the body's adrenals do, it's helpful to know the roles that the two parts of the body's adrenal glands—the adrenal cortex (the outer layer) and the adrenal medulla (the inner layer)—play. With regard to the adrenal cortex, the hypothalamic-pituitary-adrenal (HPA) cortex doesn't function of its own accord; rather, the hypothalamus signals the pituitary gland to secrete hormones (the important one, in this context, being adrenocorticotropic hormone, or ACTH) that control the adrenal cortex's output. The cortex itself is further broken down into three microscopic layers or zones. Based on the unique enzymes located in each of these zones, they secrete different hormones that have various effects in the body. They are: *Zona glomerulosa*—This outermost layer produces the hormone aldosterone, which helps regulate the body's blood pressure and protects the sodium/potassium balance within each of the body's cells—a balance that allows cells to survive, divide, and remain intact. The body can't survive without this hormone; *Zona fasciculata*—This middle layer churns out cortisol. The body's body relies on a certain amount of cortisol coursing through the body's bloodstream in order to maintain the body's circadian rhythms (more on that in a moment) and mobilize stored fats, proteins, and carbohydrates from the body's cells when the body need them for fuel. The *zona reticularis* is the innermost layer that produces dehydroepiandrosterone (DHEA), a precursor to androgens/estrogen and testosterone in men and women. In women, 90 percent of our testosterone is manufactured from DHEA in this part of the adrenals. This hormone is crucial in both men and women for maintaining and building fat-frying muscle mass, boosting the body's libido, supporting energy, protecting the skeleton, and safeguarding mental health and cognitive function as the body ages.

The inner layer of the adrenal gland, the adrenal medulla, is the control center for the body's fight-or-flight response. The hormones it puts out set off the body's physical response to stress. When stressed, the adrenal medulla sends norepinephrine into the bloodstream, which restricts blood vessels and increases blood pressure. Meanwhile, epinephrine (a.k.a. adrenaline) boosts the body's heart rate and directs blood flow away from the body's organs and toward the body's muscles.

Further, every gland in the body maintains its own circadian rhythm throughout the day. There are times when the glands are more active and times when they are at rest. This is what the science of chronobiology addresses. While most of these rhythms are barely noticeable, it's impossible to ignore when the body's adrenals are off or out of balance. When they're functioning normally, the adrenal glands are most active between 8 A.M. and 8 P.M., with a big surge to wake the body up in the morning and another key surge midday. It's no surprise why they evolved this way, as adrenal glands are in sync with the sun so that the body has the most energy during daylight and winds down when the sun sets. However, with chronic stress, the body is often asking the adrenals to secrete cortisol during parts of the day when it would normally be dropping off. The body adapts and, over time, the cortisol surges come later and later. One of the very first indications of adrenal fatigue is when the body has become a night owl and has difficulty falling asleep.

Therefore, it becomes necessary to sooth stress naturally. There are two kinds of stressors: internal and external. Internal stressors are those that disrupt the body's normal, healthy patterns and cause mismanaged blood sugar, inadequate sleep, lack of physical activity, and even the absence of orgasms. External stressors are those that occur outside of the body's body but have a real physiological and psychological impact on well-being. The method, process, and/or software of the present disclosure is configured to algorithmically calculate, based on user inputs such as period start/end dates and symptoms, treatments or action plans to minimize the toll stress takes on the body's stress response and overall health. For example, the innovation of the present disclosure may be configured to calculate, based on user inputs and algorithmic calculations, when the user is entering a hypoglycemic situation, and in response to this calculation or determination, the innovation may prompt the user to eat a specific meal calculated to rebalance the glycemic index before the body reaches a critical stage where multiple imbalances are created.

Another data input that may be used by the innovation of the present disclosure is the characteristics of the body's pathways of elimination or bowels. For example, when the body's pathways of elimination are congested, the body cannot get rid of toxins (such as endocrine-disrupting blockers) as well as the natural buildup of hormonal by-products that occur with normal metabolism. The body generally has four pathways of elimination, as the bowels or stool isn't the only way the body's body gets rid of toxins. The liver and large intestine are primary pathways. Consider the liver and large intestine as the body's internal garbage processors, compacting and moving the big stuff such as digested food, toxins, chemicals, and hormonal waste every day. The liver's primary purpose is to convert fat-soluble toxins into water-soluble waste through a two-step process so that the body can excrete them via sweat, urine, and bowel movements. Toxins include chemicals in the body's diet and environment, such as pesticides, insecticides, dry-cleaning chemicals, alcohol, cosmetics, and household cleaning products, as well as hormonal waste, that is, hormones the body's body has already used and needs to get rid of. Hormones are fat-soluble because that allows them to stay in the body longer; if they were water-soluble, the body would eliminate them all the time and they'd never have a chance to carry out their job.

The liver is responsible for moving hormones along once they've fulfilled their duty and in the first phase of detoxification, the liver breaks down fat-soluble toxins into multiple components using nutrients such as glutathione, B vitamins, and C vitamins, which are generally the nutrients stored in the liver from the foods. These multiple components, called free radicals, become more toxic as a whole than the original toxin the liver broke down in the first place. Due to this toxicity, it's essential that the second phase of detoxification kick in as quickly as possible; the goal is to minimize the damage these free radicals could do if they stuck around too long. In the second phase, selenium and amino acids in the liver combine with these free radicals to make them harmless and water-soluble. Ideally, once the liver transforms a toxin from a fat-soluble to a water-soluble molecule, it enters the gall bladder, mixes with bile, and leaves the body via the large intestine. The last thing required to complete this journey is an adequate source of dietary fiber in the large intestine to bind with the waste to make sure it leaves quickly.

Given the liver's two phases of detoxification and the necessity of ample fiber to properly eliminate toxins from the body's body through the large intestine, it becomes apparent how critical it is for body balance to have adequate dietary intake of these micronutrients. Studies have found that the body can't simply supplement with glutathione, vitamin B, vitamin C, amino acids, or selenium and expect the organs of elimination to function optimally. However, the innovation of the present disclosure also notes that, for example, prescribing vitamin C via grapefruit is not helpful for detoxifying the liver, as grapefruit also contains another enzyme that slows the liver's detoxification process. These nutrients don't readily become bioavailable when the body take them as supplements; if the body eat them as they naturally occur in foods, the body can more easily recognize them. Not only is it important to consume enough just so these organs work in the ways that they should; it's also critical to support both phases of detoxification, because if the body is lacking in the nutrients required for phase 2 the body risks exposing itself to a greater degree to the toxins that the liver created in phase 1.

The method, process, and/or software of the present disclosure may use the information related to the body's pathways for waste elimination as a data or symptom input that is considered in the diagnosis and treatment recommendations for the user. Specifically, if a user enters a symptom or data point that relates to a pathway of elimination, i.e., constipation at certain times of the day, then the innovation of the present disclosure may use this input to algorithmically calculate an approximation of the bodies increase in toxins, hormones, and other substances that imbalance the bodies endocrine system. The innovation may further algorithmically calculate a proposed treatment or recommendation to the user that will address the body's increased toxin or hormone levels or the constipation issue so that the body may return to a balanced endocrine system state as soon as possible.

The last place the body sees the endocrine balance being successful, the final phase of the innovation, is when the body first awakes in the morning, the innovation will generally recommend hydration and attempt to relieve pathways through a bowel movement after brief exercise. This routine may be recorded by the innovation through user data inputs so that patterns, diagnosis, and treatments can be algorithmically determined and recommended. For example, if a user requires longer in the morning before a bowel movement or if a cup of coffee is needed, then the user may enter this data into the innovation so that it can be analyzed in conjunction with the totality of data to determine a recommended treatment. An additional example of the innovation considering multiple data points that are not currently possible to assimilate in recommending treatment, the body's liver goes into self-cleaning mode from about 3 P.M. to about 3 A.M. The first bowel of every day movement should happen soon after walking a reasonable distance, because the liver has been working for the past twelve hours to get rid of yesterday's waste. Many people don't realize that constipation is more than a simple annoyance. The lining of the large intestine is osmotic in nature, meaning that things can travel in and out through the membrane. If the body doesn't have an efficient transit time because the liver or large intestine is congested or the body is lacking the necessary nutrients for them to perform their functions efficiently, the toxins and other chemicals working their way through this pathway can become reabsorbed into the bloodstream and continue circulating throughout the body. It's essential that all toxins and hormones be removed, and quickly. In particular, if the body is not metabolizing, breaking down, and removing estrogen as efficiently as possible, an excessive amount will accumulate in the bloodstream and lead to menstrual, fertility, and libido issues. Each of these conditions are monitored by the innovation of the present disclosure and if the user enters a symptom indicative of this issue, then the innovation of the present disclosure will algorithmically calculate a treatment protocol to remedy the constipation and the resulting hormone imbalance as quickly as possible.

The skin is the body's largest organ, so it's also, naturally, the largest organ of absorption and elimination. It has to handle whatever the large intestine and liver are unable to eliminate. It does so by excreting waste, to the best of its abilities, via sweat. This is evident when a person is stressed or upset, as the body sweat often has an unusual odor. This is an indicator that the body's pathways of elimination are congested and the skin is trying to dispel the toxins that the body's other organs couldn't handle. The skin is the last place symptoms show up when the body is experiencing elimination issues. If the body develops cystic acne, rosacea, or eczema, it's often a sign that the other systems haven't been working well. Similarly, the skin absorbs chemical and toxins it is exposed to, so it is advisable to avoid topical creams and other treatments (most of which only complicate the problem anyway) for these skin issues and instead follow a four-day cleanse that will help decongest the liver and large intestine. Watching the body's skin clear up is one of the most obvious ways of understanding just how much control a person has over making sure the body's pathways of elimination are open and clear.

The condition or status of the skin is another data point or symptom input that may be used by the innovation of the present disclosure to algorithmically diagnose and recommend treatment for conditions that result in an endocrine system imbalance. The algorithmic calculation may utilize various data and symptoms entered by the user from both recent inputs and historical data on the user to recommend an appropriate treatment option. For example, a user may input a symptom of increased sweat and odor during the day. The innovation of the present disclosure will combine this symptom input with other symptom inputs to determine, for example, that one or more pathways of elimination are slow and or blocked, which is resulting in increased toxins and hormones in the body or bloodstream. The treatment, for example, may be a detoxification cleansing routine, modified diet regimes to relieve constipation, and/or reduced hormone inputs (nutrition and otherwise) to the body until such time that the pathways of elimination can be reestablished on a normal schedule.

The lymphatic system is a network of organs, nodes, ducts, and vessels that produce and transport lymph, a fluid made up of white blood cells. This network is a major component of the body's immune system. Most people will not automatically associate the lymphatic system with elimination as one would the liver or the skin, but it plays a huge role in detoxing the body. The lymphatic system sweeps up metabolic waste, toxins, dead cells, and excess fluid from the body's organs and deposits them into the body's bloodstream, which eventually transfers them to the liver and large intestine. But if the body's lymphatic system becomes clogged or slowed, the organs and parts of the body's body that normally deposit their waste into it become backed up and blocked also.

When working efficiently, the body's lymphatic system directs white blood cells to germs and other invaders and helps the body fight off infections. But when it's congested, the lymphatic system has the opposite effect: the fluid attracts these same viruses and bacteria and transports them throughout the body, dumping them into the body's bloodstream, and putting the body at even greater risk of infection. People with lymphatic congestion issues are also likely to experience inflammation-related conditions such as allergies, high blood pressure, and chronic sinusitis, and they can develop autoimmune conditions such as rheumatoid arthritis and lupus. As such, another input that users may provide to the innovation of the present disclosure is symptoms related to the current status or effectiveness of lymphatic system. These inputs may be algorithmically processed with current and historical data by the innovation of the present disclosure to generate a treatment plan configured to remedy any issues with the effectiveness of the lymphatic system so that proper endocrine system imbalance may be restored.

Body weight is another data point that the innovation of the present disclosure may receive as an input and used to algorithmically calculate treatment plans. Body weight is an important issue for everyone, and generally the root of the problem lies in the body's liver. As noted above, the liver is responsible for removing toxins from the body, and it does this by turning fat-soluble toxins into water-soluble ones so they can be excreted through the body's large intestine, kidneys, and skin. When the body has a hormonal imbalance or problem, however, the body's liver's function is compromised (often because the body's pathways of elimination are clogged). This means that the body's liver doesn't work as efficiently as it should and thus is unable to remove toxins as rapidly as they build up. The body's body copes with this problem by storing those fat-soluble toxins in fatty tissue. For the moment, this protects the body's liver because it minimizes the toxic load there. The problem, however, is that it becomes even more difficult to shed weight. The body's fat cells don't want to let go of those toxins, because the body's body knows that doing so would pollute the body's bloodstream and create a toxic environment for the body's organs, including the body's heart and the body's brain. Thus, the body's fat cells cling to the toxins and the body clings to the body's fat cells.

Fortunately, there's a way to get the body's body to release its white-knuckled grip on the body's fat: up the body's dietary and supplemental forms of intake of vitamin A, vitamin B, and vitamin C, as well as sulforaphane and the antioxidant glutathione—nutrients the body's liver needs to detoxify effectively. By helping the body's liver do its job properly, the body will prevent those toxins from becoming backlogged and wreaking havoc on the body's waistline. The innovation of the present disclosure receives the users weight, height, and other parameters as inputs to determine things like body mass index and other parameters related to the quantity or volume of fatty cells being retained by the body.

These inputs may then be used to algorithmically determine a treatment plan that may dynamically address the cause of the problem and assist to restore the endocrine systems balance. For example, the innovation of the present disclosure may receive an input from a user indicating that the user's weight is increasing slightly during a time. When the body would not be expected to retain additional fatty cells. The innovation may dynamically calculate through an algorithmic process using both the current data and historical data on the user, a treatment plan that involves adding or increasing one or more supplemental vitamins that are calculated to target the release of toxins from fatty cells so that the body may naturally reduce its fatty cell content and therefore weight. Again, the innovation of the present disclosure will make this recommendation based upon current and historical data, thereby maintaining endocrine system balance. This is substantially distinct from other methods or treatment plans that simply increase a particular nutritional or dietary supplement to target fatty cells at times when it may not be necessary or in fact may be harmful to release toxins from fatty cells. The present innovation, via dynamic algorithmic calculations based on both current and historical data, is able to recommend when it's most appropriate for both the body and the body's endocrine system balance to take specific supplements to reduce fatty cell toxin quantities.

Each of the above noted data points, inputs, or symptoms are parameters that the innovation of the present disclosure may receive from a user. These inputs are then stored by the innovation of the present disclosure for use in future diagnosis or treatment plans as historical data. The user inputs this information via an initial set up to start with, which includes providing a plurality of information to the innovation of the present disclosure. Thereafter, the user is allowed to and is prompted to input symptoms or body conditions on a daily and even hourly basis. As such, the user regularly interacts with the innovation of the present disclosure by providing input there too. The input generally constitutes information on the current condition of the user's body. These inputs may be as simple as a mood or a feeling of being tired, or may be as complex as medical symptoms such as abdominal pain, vaginal discomfort, period characteristics, characteristics, or otherwise.

What a user initially creates a profile via the innovation of the present disclosure, the innovation receives the information and generates a baseline treatment profile for the user. The baseline treatment profile is a general first start to managing the endocrine system hormone balance. For example, the baseline profile begins with establishing period tracking, duration, quality, and dates. This information may be used to generate a baseline treatment plan for the user, however, as the user enters daily information into the innovation, the baseline treatment plan will be algorithmically modified by the innovation of the present disclosure to provide a more up-to-date and accurate treatment plan based upon the most recent data or symptoms entered by the user along with the user's historical data.

The algorithmic calculations noted above may generally include processing the users input with a microprocessor-based system running a software package that is stored on a computer readable media. The software package may generally be configured to assess the user's current symptoms to determine a possible diagnosis and treatment. Further, the algorithm may also incorporate the user's historical data into the algorithm to determine a treatment. Historical data is relevant in that it can eliminate treatment plans that have been tried in the past unsuccessfully. Further, historical data may be used to validate a proposed treatment plan in that it may have been used previously in a successful manner. Similarly, historical data may be used by the algorithm of the present innovation to identify trends in treatment plans to avoid unnecessarily incorporating elements into a treatment plan that may further imbalance the endocrine system.

The user inputs may also be used by the innovation of the present disclosure to algorithmically calculate and recommend a nutrition plan to the user. The innovation of the present disclosure may access the various nutritional databases having foods, nutritional supplements, and other items stored there in to select specific items meeting nutritional requirements to be used in a nutrition plan for the user. The nutrition plan may be initiated as a baseline plan and then modified on a daily or even hourly basis to address or accommodate user inputs or symptoms that can be corrected by nutritional changes.

The innovation of the present disclosure may also generate a calendar representing a woman's menstrual cycle that may be displayed to the user. The innovation may allow a user to input a start date, end date, and an average length of menses, which the innovation may then use to calculate the user's ovulation date and to predict the days, phases, and other period related information. More particularly, the calendar functionality of the present innovation may calculate each of the four phases of a woman's menstrual cycle based upon the user input initially received, which may be previous period information, along with and current or historical data on the user, such as current symptoms or previous treatments related to the woman's menstrual cycle, so that the most accurate cycle information may be calculated, input into the calendar, and presented to the user. The cycle schedule may be a primary graphical user interface for the user in the form of a calendar whereby the various stages of the cycle may be displayed to the user using color-coded indicators. Further, the user may view a calendar day either in the past or in the future and see the recommendations made by the innovation of the present disclosure for that particular day. For days in the past, the innovation will present symptoms that were stored from that day, treatment plans, diagnosis, and other information calculated by the innovation of the present disclosure. For a day selected in the future, the innovation of the present disclosure may present predictive information on the user cycle, anticipated mood, recommended physical activity, recommended nutrition, intimacy recommendations, and other physical and mental attributes that the user may find helpful in scheduling daily activities such as meetings for their job, social interactions, or romantic encounters.

The user inputs may also be used to conduct a targeted advertising methodology. For example, specific user inputs at specific times of a woman's cycle (phase) may be used to trigger and deliver targeted advertising messages to the user. The determination of who receives advertising messages and what messages to present may be algorithmically calculated in accordance with a predefined algorithm. The algorithm may, for example, be configured to review a user's symptoms to identify a particular symptom associated with an advertising message and then present the advertising message to the user if the symptom is entered by the user. Similarly, for example, advertising may be delivered to users based on time, calendar dates, or phases of a woman's cycle. For example, any woman that enters into a predefined phase of her menstrual cycle may be presented with a predetermined advertisement related to that phase of her cycle.

As an example of how the innovation may calculate parameters of the woman's cycle, the cycle length minus period length divided by two may be used to determine the number of days between periods (X). Similarly, the follicular phase will follow the menstrual phase with a duration (in days) of X/2, the ovulation phase will follow follicular phase and will have a duration (in days) of X/2, and the luteal phase will follow ovular phase with a duration of X. Further, assuming a cycle length of 28 days and a period length of 5 days is inputted by the user, then the innovation of the present disclosure would calculate X=(28−5)/2=11.5 and X/2=5.75. Similarly, with a cycle length of 29 days and a period of 7 days, X=(22/2)=11 and X/2=5.5. In cases where the calculated days are not whole numbers, then the innovation will round the calculated result to a whole day result as follows: In the follicular phase, round 0.5 and above up to the nearest whole number (F); in the ovulation phase round 0.5 and below down to the nearest whole number (O); and the luteal phase is calculated as the cycle length minus the period length minus the follicular phase calculated length (F) minus the ovulation phase calculated length (O). Thus, the innovation of the present disclosure operates to dynamically adjust the timing of each phase of a woman's cycle based upon user input.

The innovation of the present disclosure may also determine if the menstrual phase portion of the cycle is within the expected normal range, and if so, the innovation may assign start and end dates for each of the three phases. For example, if the menstrual (M) value is outside the expected normal range, then the algorithm adjusts the values of the date ranges for the next three phases to fit a standard cycle length. This is step one of the calculation. A data look up table is accessed to provide a starting point for dietary and other lifestyle changes based on these calculations and the other symptoms imputed by the user. Similarly, the present innovation may use the following equations:

$$\text{Initial condition}=(C+M)+X+Y+Z; \text{ and} \quad (1)$$

$$\text{Second input}=(C+M)+X+Y+Z, \quad (2)$$

where M=Menstrual; F=Follicular; O=Ovulation (day 1 of bleed+14); L=Luteal; C=user input; W=Standard Menstrual length; X=Standard F length; Y=Standard O length; Z=Standard L length; Other=A list of other symptoms being experienced by the user; and M is the end date input from user.

The innovation may then determine if the menstrual phase portion is within the expected normal range, and if so, assigns start and end dates for each of the next three phases. If the M value is outside the expected normal range then the algorithm adjusts the values of the date ranges for the next three phases to fit a standard cycle length. In the first step of the data calculation a data look up table is accessed to provide a starting point for dietary and other lifestyle changes based on these calculations and the other symptoms imputed by the user. For phase 2 and subsequent phases the "Refined Other"=A list of other symptoms being experienced by the user, wherein:

$$\text{Refined input}=(C2+M)+X+Y+Z, \text{ where } M \text{ is the start date input from the user; and} \quad (3)$$

$$\text{Refined Second input}=(C3+M)+X+Y+Z, \text{ where } M \text{ is the end date input from user.} \quad (4)$$

The innovation of the present disclosure may also calculate the user specific cycle length based on the two data sets (Initial and refined) where the total length may differ from the expected normal range and adjust each of the remaining three phases accordingly. Based on the new values and the refined other symptoms inputs from the user, a lookup table is accessed to present the user with new recommendations for dietary and lifestyle changes. This process repeats each cycle and the specific values continue to be dialed in dynamically along with the user specific treatment guidelines.

Embodiments of the disclosure provide for the innovation to allow users to track symptoms. For example, as a user moves from one phase of the cycle to the next, the innovation asks the user to choose from predetermined phase specific symptoms and select which symptoms they are experiencing in the current phase. The innovation stores the inputted information as current symptoms, but also stores the information as historical information that may be used for future diagnosis and treatment recommendations based on historical data. As such, the innovation of the present disclosure presents the user with a standardized set of symptoms that are relevant to the phase they're in, and based on user input, and based on their phase, we refer to a look up table and present them with the appropriate recommendation.

The innovation of the present disclosure also gives users insight into the cause(s) of each symptom and corresponding dietary fixes. For any symptom a user is having, they can process through the innovation to learn the functional medicine root cause explanation as to why they are having that symptom and they are given food suggestions to address that root cause naturally. Further still, the innovation of the present disclosure algorithmically logs recurrent symptoms and provides a four-week diet plan for recurrent symptoms. The diet plan is determined by the innovation of the present disclosure accumulating a list of foods calculated to treat or address the user's identified symptoms. Therefore, as a user moves through several cycles and logs which symptoms she has in each phase of her cycle, the innovation will reflect back to her what symptoms show patterns of consistent recurrence for her consideration. Therefore, the innovation of the present disclosure may utilize an exemplary algorithm of if a symptom occurs more than a preset number of times, then the innovation may calculate remedial nutrition recommendations and present user with a multiweek protocol configured to address the recurring symptoms. Similarly, the innovation of the present disclosure is configured to generate appropriate cycle phase-based diet, exercise, and lifestyle activity recommendations based on when a woman moves from one phase to the next based on her cycle calendar inputs. If a woman wants to address the prompt from the innovation regarding recurrent symptoms she can obtain a four-week nutritional plan to address that recurrent symptom. This is accomplished with a look up table based on their dynamically adjusted phases. The innovation may also be configured to share updates on her phase with her romantic partner. At the user's discretion, she can input the partner who will receive updates when she moves from one phase of the cycle to the next. The partner will receive emails synchronized with her calendar to provide guidance on phase optimal romantic and lifestyle activities to be shared as a couple. This is accomplished with a look up table based on their dynamically adjusted phases.

The innovation of the present disclosure may also operate to receive various inputs from the user and algorithmically calculate and recommended shopping list for the user, whereby the recommended shopping list includes a meal plan that is calculated to address specific symptoms or issues that the user is experiencing in the form of an endocrine system hormonal balance. The shopping list may also incorporate historical data on the user cycle to suggest various foods and nutritional supplements during various stages of the user cycle to optimize the user's lifestyle in conjunction with the cycle.

The innovation of the present disclosure may also operate to receive various inputs from the user and algorithmically calculate and recommend an exercise regime for the user, whereby the recommended exercise regime is based on a plurality of factors including the current stage of the user in the cycle, the user's current symptoms entered into the innovation the present disclosure, the user's historical data on cycle and hormone balance at this particular time or stage of the month, and the users current nutritional state. As the user's symptoms vary or change daily, the innovation of the present disclosure may algorithmically recalculate exercise recommendations to suit the current stage of the cycle along with the users current and predicted symptoms.

FIG. 1 illustrates an exemplary hardware configuration that may be utilized to implement various embodiments of the present disclosure. The exemplary hardware configuration includes a processor 100, which may be a microprocessor-based computer chip or other logic element capable of executing instructions stored on a computer readable media. The processor 100 is in communication with a memory 104, which may be used to store processing instructions, data that may be used by computer programs, and computer programs themselves. The processor 100 is also in communication with an input device 100 and to. The input device 102 may be any number of devices capable of receiving user or other inputs and communicating those inputs through to the processor 100. The processor 100 is also in communication with an output device 103, which may be a graphical user interface that a user may interact with. Output device 103 may also include various communication devices, such as wireless, cellular, or Internet type communication devices that will allow the processor 100 to electronically communicate with remote devices through messages, email, or other electronic signals.

In operation, one embodiment of the present disclosure may be a computer program configured to be executed by a processor to conduct the steps of the present exemplary method. For example, program instructions to support the current disclosure may be stored in memory 104. Those instructions may be read and executed by processor 100. As such, inputs from the user in the form of data, symptoms, etc. may be received on the input device 100 and to and processed by the processor 100 in accordance with the software instructions that are stored on memory 104. Upon processing the inputs in accordance with the software instructions, the processor may output the information to be communicated to the user in the form of a display output device 103.

Additionally, memory 104 may be used to store historical data received from the user or calculated by the processor 100. For example, a user is cycle, symptoms, physical characteristics, and other information may be calculated by the processor 100 in accordance with the software instructions stored on memory 104. Treatment plans and recommendations may be algorithmically generated and presented to the user via the output device 103. These treatment plans and recommendations may be stored, along with the data used to generate the plans and recommendations, and memory 104. As such, as future symptoms are entered into the software product of the present disclosure, the historical information stored in memory 104 may be accessed by the processor 100 and used to calculate current treatment plans and recommendations that are based upon not only current symptoms, but also on the user's historical medical biography. As such, the software product of the present disclosure is capable of learning from historical data which treatment plans and recommendations were successful in remedying certain conditions in a user and is able to utilize those treatment plans that were successful and seek optional treatment plans for historical treatment plans that were unsuccessful.

Figure 2:
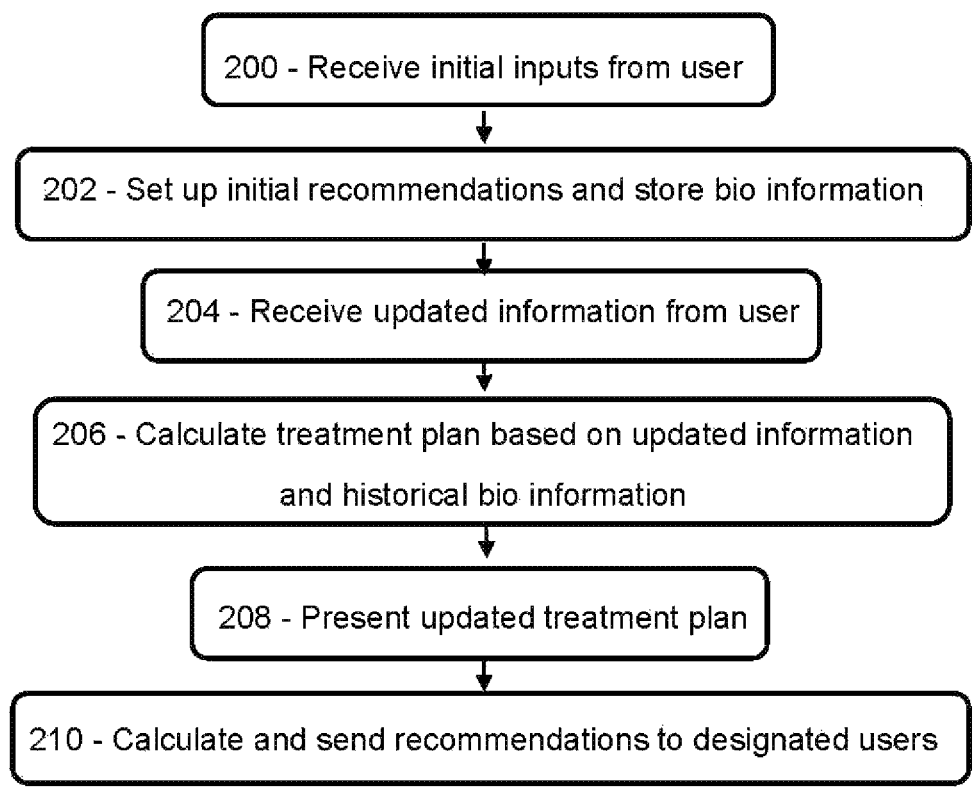
FIG. 2 illustrates an exemplary flow diagram for an exemplary embodiment of the present disclosure.

FIG. 2 illustrates an exemplary flow diagram for an exemplary embodiment of the present disclosure. The exemplary flow diagram begins at step 200 where the software package of the present disclosure receives initial inputs from the user. These initial inputs generally comprise the information required to set up the user on the software of the present disclosure and may include biographical information, statistics, dates, durations, and other information needed to set up the user on the software platform. The method continues to step 202 in the flowchart where the processor in conjunction with a software package or set of instructions stored in memory are utilized to generate additional recommendations for the user based upon the initial biographical information entered by the user. These initial recommendations may include a cycle tracking calendar, general food recommendations based upon the biographical information, exercise routines, etc.

The method continues to step 204 where the software package receives updated information from the user. Updated information generally comprises symptoms or data that were not available at the time the initial inputs were entered into the software package by the user. For example, updated information may include daily symptoms related to women's health, such as mood, discomfort, energy level, constipation, menstrual flow characteristics, skin condition, and several other conditions or symptoms both described herein and otherwise. Once the updated information is received, the method continues to step 206 where a processor, in conjunction with a memory device that contains software instructions to be executed by the processor thereon, algorithmically reviews the initial inputs, the biographical information, and the updated information from the user to generate a diagnosis and corresponding treatment plan. The method then continues to tip 208 where the treatment plan and diagnosis may be presented to the user via an output device, for example. The method then continues to step 210 where recommendations are calculated and sent to designated users, such as spouses, boyfriends, friends, or family, that the user desires to have receive the information.

Descriptions of the various exemplary embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. In particular, the inventor contemplates that any combination of the various exemplary embodiments described above may be utilized without departing from the scope of the present disclosure. Further, the terminology used herein was chosen to best explain the principles of the exemplary embodiments, the practical application or technical improvement over technologies found in the market, or to enable others of ordinary skill in the art to understand the embodiments disclosed herein.

As will be appreciated by one skilled in the art, aspects of the present disclosure may be embodied as a system, process, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

According to exemplary embodiments, one or more of the modules or program managers may be implemented in software for execution by various types of processors. An identified module or program manager of executable code may, for instance, include one or more physical or logical blocks of computer instructions that may, for instance, be organized as an object, procedure, or function. Further, the executables of an identified module (or program manager) may not be physically located together, but may include disparate instructions stored in different locations that, when joined logically together, include the module and achieve the stated purpose for the module.

The executable code may be a single instruction, or many instructions, and may be distributed over several different code segments, among different programs, and across several memory devices. Similarly, operational data may be identified and illustrated in association with one or more modules or program managers, and may be embodied in any suitable form and organized within any suitable type of data structure. The operational data may be collected as a single data set, or may be distributed over different locations including over different storage devices, and may exist, at least partially, as electronic signals on a system or network.

According to exemplary embodiments, a database, as described herein, may be any standard or proprietary database software, such as ORACLE, MICROSOFT ACCESS, SYBASE, or DBASE II, for example. The database may have fields, records, data, and other database elements that may be associated through database specific software. Additionally, data may be mapped, or associating one data entry with another data entry. For example, the data contained in the location of a character file can be mapped to a field in a second table. The physical location of the database is not limiting, and the database may be remote or distributed. For example, the database may exist remotely from the server, and run on a separate platform. Further, the database may be accessible across a local area network (LAN), a wide area network (WAN), or the Internet. It is to be understood that more than one database may be implemented or used to create a single database.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Additional examples of computer readable storage medium include but are not limited to an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access database applications or related data available in the cloud. For example, the matching application could execute on a computing system in the cloud and allow non-shared weight queries to use shared weight indexes. In such a case, the matching application could modify non-shared weight queries and store the query results at a storage location in the cloud. Doing so allows a user to access this information from any computing system attached to a network connected to the cloud (e.g., the Internet).

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The foregoing has outlined features of several embodiments so that those skilled in the art may better understand the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for diagnosing, treating, and tracking women's hormonal health, comprising:
   receiving cycle inputs from a user via an input device, the inputs representing hormonal data related to a menstrual cycle;
   receiving the cycle inputs in a processor and storing the cycle inputs in a memory in electrical communication with the processor as historical data;
   calculating an initial timing and duration of at least a follicular phase, an ovulation phase, a luteal phase, and a menstrual phase of the user's menstrual cycle using the cycle inputs;
   displaying the calculated initial timing and duration of at least the follicular phase, the ovulation phase, and the luteal phase of the user's menstrual cycle to the user on a graphical user interface;
   receiving current symptom inputs from the user via the input device, the symptom inputs being transmitted to the processor and stored in the memory;
   dynamically recalculating an updated timing and duration, with the processor, of at least the follicular phase, the ovulation phase, the luteal phase, and the menstrual phase of the user's cycle based on the current symptom inputs and historical data, the current symptom inputs being inputted at a later time than the cycle inputs utilized in calculating the initial timing and duration;
   generating, with the processor, a treatment plan to remedy conditions associated with the current symptom inputs, the treatment plan being based on the updated timing; and
   displaying the recalculated updated timing of the at least three phases of the user's cycle and the treatment plan to the user on the graphical user interface,
   wherein calculating the initial timing and duration of the first phase, the second phase, and the third phase of the user's menstrual cycle comprises:
   a) cycle length minus period length divided by two represents a number of days (X) between periods;
   b) the follicular phase is calculated to follow a menstrual phase with a duration of X/2 days;
   c) the ovulation phase is calculated to follow follicular phase with a duration of X/2 days;
   d) the luteal phase is calculated to follow ovular phase with a duration of X days; and
   e) using a standard cycle length of Z days and a period length of Y days inputted by the user, calculating X as (Z−Y)/2 days,
   wherein during the follicular phase the calculation rounds 0.5 and above up to the nearest whole number (F), in the ovulation phase the calculation rounds 0.5 and below down to the nearest whole number, and the luteal phase the calculation uses the cycle length minus the period length minus the follicular phase calculated length (F) minus the ovulation phase calculated length (O).

2. The method of claim 1, wherein the treatment plan comprises a nutritional treatment plan having specific foods corresponding to the symptom inputs and calculated to provide remedy therefrom.

3. The method of claim 2, wherein the symptom inputs comprise medical, emotional, or hormonal conditions identifiable by the user.

4. The method of claim 3, wherein the nutritional treatment plan is generated by accessing a database of nutritional elements and selecting a nutritional item that is known to remedy a specific user symptom and that is not in conflict with the historical data.

5. The method of claim 4, wherein conflict with historical data comprises a nutritional item that was previously recommended to the user and resulted in either sub-optimal symptom remedy results or other negative result to the user.

6. The method of claim 2, wherein the treatment plan comprises a physical activity plan.

7. The method of claim 1, wherein the symptom inputs are entered multiple times a day and are stored in the memory as historical data.

8. The method of claim 7, wherein every time system inputs are received the method recalculates the at least 3 phases of the user's cycle based on the symptom inputs and historical data and generates a corresponding updated treatment plan.

9. The method of claim 1, further comprising determining if a menstrual phase portion of the menstrual cycle is within an expected normal range and assigning modified start and end dates for each of the at least three phases when the cycle is outside the expected normal range.

10. A non-transitory computer readable medium comprising computer executable instructions stored thereon, that when executed by a processor, cause the processor to perform a method for diagnosing, treating, and tracking women's hormonal health, comprising:
   receiving cycle inputs in a processor and storing the cycle inputs in a memory in electrical communication with the processor as historical data;
   calculating an initial timing and duration of at least a follicular phase, an ovulation phase, a luteal phase, and a menstrual phase of the user's menstrual cycle using the cycle inputs;
   displaying the calculated initial timing and duration of at least the follicular phase, the ovulation phase, and the luteal phase of the user's menstrual cycle to the user on a graphical user interface;
   receiving current symptom inputs from the user via the input device, the symptom inputs representing medical, emotional, or hormonal symptoms related to the user's menstrual cycle, and the symptom inputs being transmitted to the processor and stored in the memory;
   dynamically recalculating an updated timing and duration, with the processor, of at least the follicular phase, and the ovulation phase, and the luteal phase of the user's cycle based on the symptom inputs and historical data, the current symptom inputs being inputted at a later time than the cycle inputs utilized in calculating the initial timing and duration;
   generating, with the processor, a treatment plan to remedy conditions associated with the current symptom inputs, the treatment plan including nutritional recommendations comprising a therapeutic treatment plan corresponding to the current symptom inputs and the updated timing and calculated to provide remedy therefrom; and
   displaying the recalculated at least three phases of the user's cycle and the treatment plan to the user on the graphical user interface,
   wherein calculating the initial timing and duration of the first phase, the second phase, and the third phase of the user's menstrual cycle comprises:
   f) cycle length minus period length divided by two represents a number of days (X) between periods;
   g) the follicular phase is calculated to follow a menstrual phase with a duration of X/2 days;
   h) the ovulation phase is calculated to follow follicular phase with a duration of X/2 days;
   i) the luteal phase is calculated to follow ovular phase with a duration of X days; and
   j) using a standard cycle length of Z days and a period length of Y days inputted by the user, calculating X as (Z−Y)/2 days,
   wherein during the follicular phase the calculation rounds 0.5 and above up to the nearest whole number (F), in the ovulation phase the calculation rounds 0.5 and below down to the nearest whole number, and the luteal phase the calculation uses the cycle length minus the period length minus the follicular phase calculated length (F) minus the ovulation phase calculated length (O).

11. The non-transitory computer readable medium of claim 10, wherein the nutritional treatment plan is generated by accessing a database of nutritional elements and selecting a nutritional item that is known to remedy a specific user symptom and that is not in conflict with the historical data.

12. The non-transitory computer readable medium of claim 11, wherein conflict with historical data comprises a nutritional item that was previously recommended to the user and resulted in either sub-optimal symptom remedy results or other negative result to the user.

13. A method for monitoring and treating women's hormonal health, comprising:
   receiving initial cycle inputs from a user representing hormonal information related to a menstrual cycle and storing the inputs in a memory as historical data;
   calculating an initial timing and duration of a follicular phase, an ovulation phase, and a luteal phase of the user's menstrual cycle using the initial cycle inputs;
   displaying the calculated initial timing and duration of the follicular, ovulation, luteal, and menstrual phases a graphical user interface;
   receiving current symptom inputs from the user representing medical, emotional, or hormonal symptoms related to the user's menstrual cycle, and the symptom inputs being transmitted to the processor and stored in the memory;
   dynamically recalculating an updated timing and duration of the follicular, ovulation, luteal, and menstrual phases of the user's cycle based on the current symptom inputs and historical data, the current symptom inputs being inputted at a later time than the initial cycle inputs;
   generating a treatment plan to remedy conditions associated with the current symptom inputs, the treatment plan including nutritional and physical activity recommendations comprising a therapeutic protocol based on the updated timing and corresponding to the current symptom inputs and calculated to provide remedy therefrom; and displaying the updated timing of the follicular, ovulation, and luteal phases of the user's cycle and the treatment plan to the user.

14. The method of claim 13, wherein:
the therapeutic protocol includes at least one of a specific food, an exercise, or a nutritional supplement.

* * * * *